United States Patent [19]

Spencer

[11] Patent Number: 4,523,969
[45] Date of Patent: Jun. 18, 1985

[54] METHOD AND APPARATUS FOR MANUFACTURING A PRODUCT HAVING ELASTIC MEANS DISPOSED IN A DIRECTION TRANSVERSE TO PRODUCT MOVEMENT

[75] Inventor: Harvey J. Spencer, Green Bay, Wis.

[73] Assignee: Paper Converting Machine Company, Green Bay, Wis.

[21] Appl. No.: 569,172

[22] Filed: Jan. 9, 1984

[51] Int. Cl.³ .............................................. B32B 31/10
[52] U.S. Cl. ..................... 156/161; 156/164; 156/229; 156/265; 156/301; 156/519; 156/502
[58] Field of Search ............... 156/161, 164, 229, 552, 156/519, 567, 568, 300, 301, 764, 517, 494

[56] References Cited

U.S. PATENT DOCUMENTS

| | | | |
|---|---|---|---|
| 4,240,866 | 12/1980 | Rega | 156/519 |
| 4,284,454 | 8/1981 | Joa | 156/229 |
| 4,285,747 | 8/1981 | Rega | 156/164 |
| 4,379,016 | 4/1983 | Stemmler et al. | 156/164 |
| 4,397,704 | 8/1983 | Frick | 156/201 |
| 4,417,938 | 11/1983 | Sigl | 156/229 |

*Primary Examiner*—Michael Ball
*Attorney, Agent, or Firm*—Tilton, Fallon, Lungmus & Chestnut

[57] ABSTRACT

Method and apparatus for applying stretched elastic segments to a web as for a diaper waistband and the like which include advancing a stretched continuous elastic ribbon, gripping the ribbon at two pairs of points, severing the ribbon between the gripped pairs to provide a stretched segment and advancing the ribbon segment in planetary fashion to unite the same to a continuous web.

15 Claims, 11 Drawing Figures

METHOD AND APPARATUS FOR MANUFACTURING A PRODUCT HAVING ELASTIC MEANS DISPOSED IN A DIRECTION TRANSVERSE TO PRODUCT MOVEMENT

BACKGROUND OF THE INVENTION

There is plentiful prior art for methods and apparatus that attach stretched elastic ribbons at predetermined intervals to a relatively inelastic web material that is subsequently cut into discreet articles. The elastic ribbon is applied in the direction of web movement and hence the elastic functions to gather intermediate portions of the article, for example, portions of a disposable diaper that are adjacent to an infant's legs.

This field of prior art also includes methods and apparatus for applying discreet segments (instead of ribbons) of elastic to predetermined portions of a moving web for subsequent cutoff, again with the same function, but without the non-stretched excess elastic ribbon that extends beyond the predetermined bonded region.

Typical of the first approach involving a continuous ribbon are U.S. Pat. Nos. 4,081,301; 4,240,866; and 4,239,578. Other teachings relating to the application of discreet segments of stretched elastic to a moving web include U.S. Pat. Nos. 4,379,016 and 4,397,704.

The problem of applying a stretched continuous (or segmented piece) of elastic in a transverse direction to a moving web becomes much more complicated. One approach is suggested in U.S. Pat. Nos. 4,240,866 and 4,285,747 whereby an elongated web substrate is "gathered" at one or more locations in a direction transverse to web movement and, while the web is looped or gathered, applying nonstretched elastic ribbon on adjacent and outward marginal edges with the elastic bridging the transverse loop. At a point downstream, the gathered loop in the narrowed web is removed by stretching the web in a transverse direction, and when the connected series of articles are severed and put to use, the stretched elastic in the non-gathered article acts to cause selective transverse gathering. Another method and apparatus for applying elastic bands transversely to a moving web is shown in U.S. Pat. No. 4,284,454 albeit differences of function and use.

In the prior art method and apparatus of '454, parallel elastic ribbons are fed, cut off, and transported at right angles prior to adhesive placement and attachment to the continuously moving web. However, the right angle transposition involves transfer of the stretched elastic segments from one set of grippers to a second set of grippers, and also involves indexing movement of the conveyor having the first gripping means.

SUMMARY OF INVENTION

This invention differs from the prior art in teaching a method and means to transport a stretched and discreet elastic ribbon segment while changing directions 90° but without transferring from a first gripping means to a second gripping means. Further, by the unique arrangement and methods involved, feeding, cut off, right angle transport, and application of the stretched elastic segments to the moving web are all accomplished with rotary motion and the benefits of better registration at higher speeds.

This invention deals with a method and means to apply stretched elastic segments aligned in a transverse direction to a moving web such that after the moving web is cut into discreet articles, portions thereof corresponding to waist bands will tend to gather such that the article retains a snug elasticized fit around the wearer's waist. Thus, highly functional disposable diapers can include elasticized waist bands as well as elasticized leg portions, and according to the invention, the elasticized waist band can include segments of any predetermined length, (not necessarily full width) applied in continuous motion at high operating speed.

By arranging grippers in co-operating, intermittently aligned fashion and accelerating the same selectively in one portion of an orbit, the pre-stretched elastic bands can be integrated to the plastic web constituting ultimately the outer layer of a diaper.

DESCRIPTION OF THE DRAWINGS

FIG. 2 illustrates that the inventive device includes six transfer arms rotatable about a central hub and axis. However, for clarity, illustrations hereinafter show only one transfer arm and the mechanisms associated therewith.

DESCRIPTION OF THE INVENTION

Overall Operation

Figure 1:
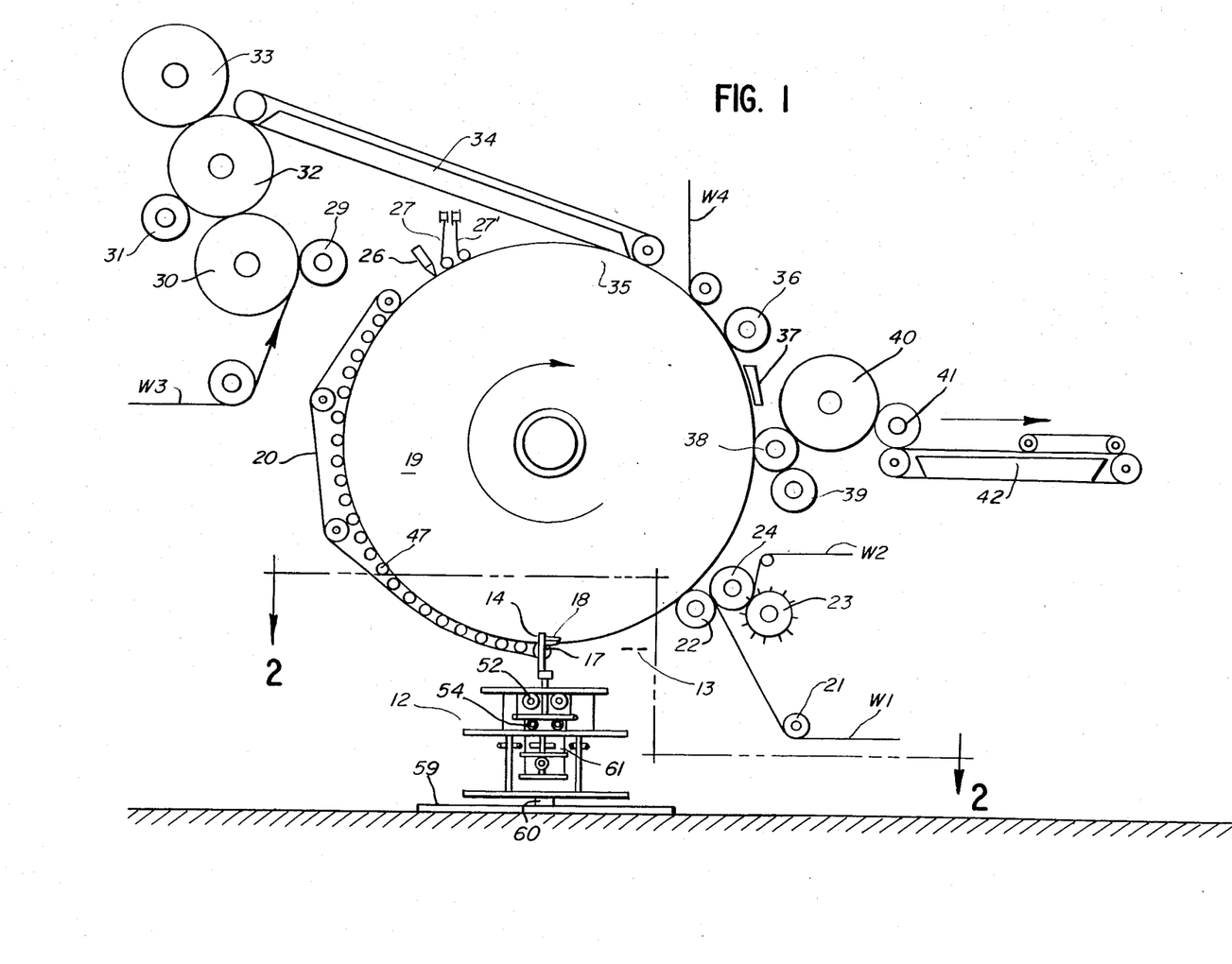
FIG. 1 is a side elevation illustrating the inventive device in cooperating relationship to a sealing drum—both shown as a portion of a diaper assembly line.
Figure 2:
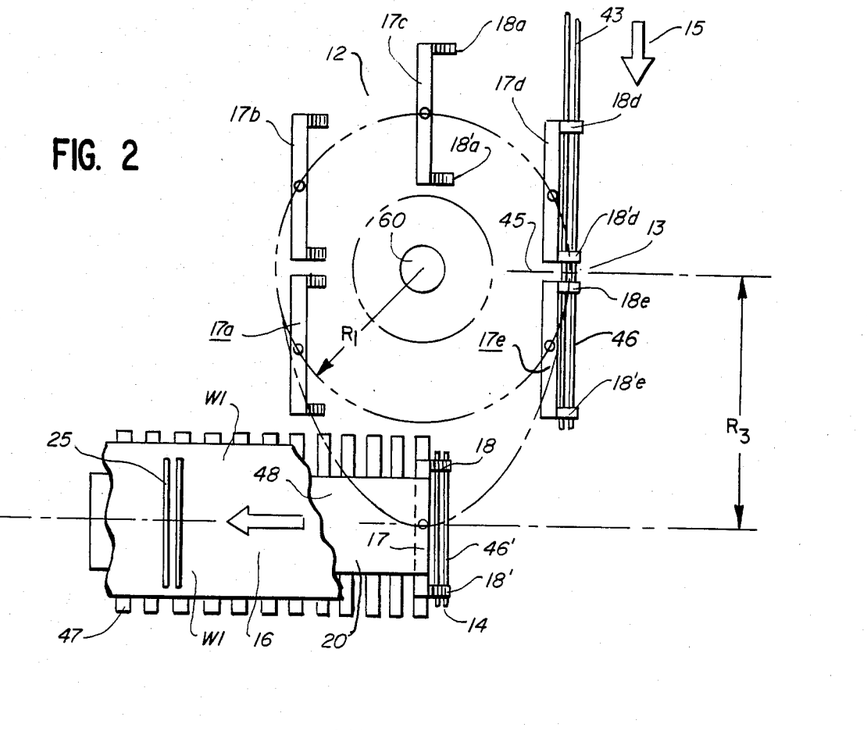
FIG. 2 is a plan view of the elastic ribbon transfer device as viewed along line 2—2 of FIG. 1—drum portion removed.

In FIG. 1, the inventive elastic ribbon transfer device 12 moves a pair of parallel, previously stretched elastic ribbon segments from an infeed position 13 perpendicular to the normal flow of web materials to a transfer position 14—see also FIG. 2. In other words, two sets of grippers (see the right hand portion of FIG. 2) are aligned so that when the ribbons are severed between grippers, the tensioned or stretched condition is retained—in both sets of grippers. In movement from position 13 to position 14 the stretched elastic segments undergo two primary transitional movements, i.e., a 90° transfer from incoming direction 15 to outgoing direction 16, and continuous motion at a radius $R_1$ when at the incoming position 13, and after right angle translation, movement of the elastic ribbon at a higher velocity and at radius R₃ when at the transfer point 14. The increase of radius $R_1$ to $R_3$ allows elastic ribbons of, for example, 6" to 20" stretched length to be placed, for example, at 12" to 36" spaced intervals on web material moving perpendicularly to the infeed orientation of the elastic ribbon. In FIG. 1, a gripper assembly 17 is shown at transfer position 14, and at this instant, a pair of ribbons stretched between two gripper means 18-18' (see FIG. 2) are introduced into the nip between vacuum drum 19 and co-acting belt system 20.

Prior to transferring the stretched elastic ribbons, a continuous plastic web $W_1$ passes over guide roll 21 and lay-on roll 22. Tape segments from tape web $W_2$ are cut to short lengths by tape cutoff roll 23 and transferred to the plastic web via tape applicator roll 24. The plastic web $W_1$ with tape segments is thus entrained on the bottom surface of vacuum drum 19 and, when reaching position 14, will be joined by the pair of stretched elastic ribbons being transferred from gripper assembly 17.

By the time vacuum drum 19 rotates to a position under adhesive applicator 26, the pair of stretched elastic ribbons (see 25 of FIG. 2), and continuous plastic web $W_1$ will be effectively bonded together. In FIG. 1, additional elastic strips 27, 27' are added and sealed to plastic web $W_1$ and ultimately become the longitudinal elastic gathering means adjacent the wearer's legs. Further downstream on the surface of rotating drum 19, discreet spaced fluff pads 28 are introduced. They are processed from incoming continuous fluff web $W_3$ which travel between nip roll 29 and transfer roll 30 before being cut by roll 31 and placed in spaced arrangement on vacuum roll 32 which coacts with a die roll 33 to contour the fluff in hourglass shape before being transferred by vacuum box 34 onto the surface of vacuum drum 19 at position 35. Subsequently, a continuous nonwoven web $W_4$ is added and is sealed to the plastic web $W_1$ in spaces between and marginally outward of the contoured fluff pad. A contoured bumper roll 36 and tape folding shoes 37 essentially complete the assembly of plastic, tape tabs, fluff, nonwoven and both the transverse stretched elastic as well as the longitudinal stretched elastic prior to subsequent cut out of excess plastic and nonwoven materials through anvil roll 38, cutoff die roll 39, and finally cutting the continuous and assembled web into discreet articles between knife roll 40, anvil roll 41 and final transfer by vacuum box 42 to downstream stacking, counting and packaging operations.

Detailed of Ribbon Transfer

FIG. 2 is a plan view of the stretched elastic ribbon transporting apparatus. Details of the inventive mechanism follow, but FIG. 2 is intended to illustrate the operation and its immediate environment. Reference to FIG. 2 reveals that a plurality of gripper assemblies (six as illustrated) 17 through 17e are mounted to rotate in a horizontal plane about a vertical axis. In a 90° quadrant of this rotation (lower right in FIG. 2), the incoming stretched elastic ribbon pair 43 is continually fed in the direction of arrow 15.

When two consecutive gripper assemblies reach the positions of 17d and 17e, both pairs of grippers 18d'-18d" and 18e-18e' close to entrap the parallel pairs of ribbons and at this instant, a cutoff knife or blade 44 of FIG. 4 passes through gap 45 to sever the continuous ribbon pair 43 into segments 46 which are subsequently moved to the transfer position 46' and 14.

The lower portion of FIG. 2 is viewed outwardly from the surface of drum 19 (drum removed) and shows various individual rollers 47 of belt system 20 (see FIG. 1) supporting a belt 48 which is narrower than the space between gripper pair 18-18', etc. Belt 48 and back up rollers 47 coact to force the plastic web $W_1$ and spaced pairs of stretched elastic ribbons 25 against the surface of vacuum drum 19. Adhesive can be printed on the plastic web $W_1$ in regions directly underlying the elastic ribbon segments or alternately, can be printed or extruded onto the incoming elastic ribbon—intermittently being preferred to avoid fouling the grippers. Once a proper seal is established between the stretched transverse elastic ribbon and the underlying plastic web $W_1$, the article with transverse elastic ribbons is completed according to the steps described hereinabove.

Figure 3:
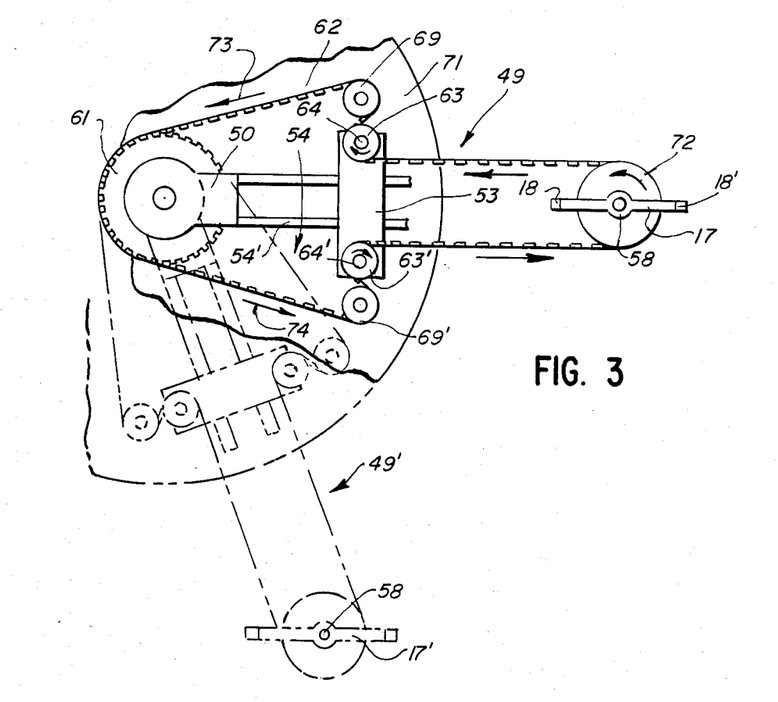
FIG. 3 is a schematic plan view showing how the gripper assemblies maintain a fixed attitude relative to the machine frame.

In FIG. 2 it is noted that regardless of rotational position, for example, 17, 17a, 17b, 17e, etc., the gripper assembly 17 is always parallel to the direction 15 of incoming ribbons 43. The mechanism in FIG. 3 shows how undirectional orientation of the gripper is maintained despite rotation. Since FIG. 3 is somewhat schematic, various mechanisms and shapes may not agree with subsequent illustrations; however, like numbers are maintained where the same function part is subsequently described.

Transfer Rotating Mechanism

To Maintain Fixed Orientation

Figure 10:
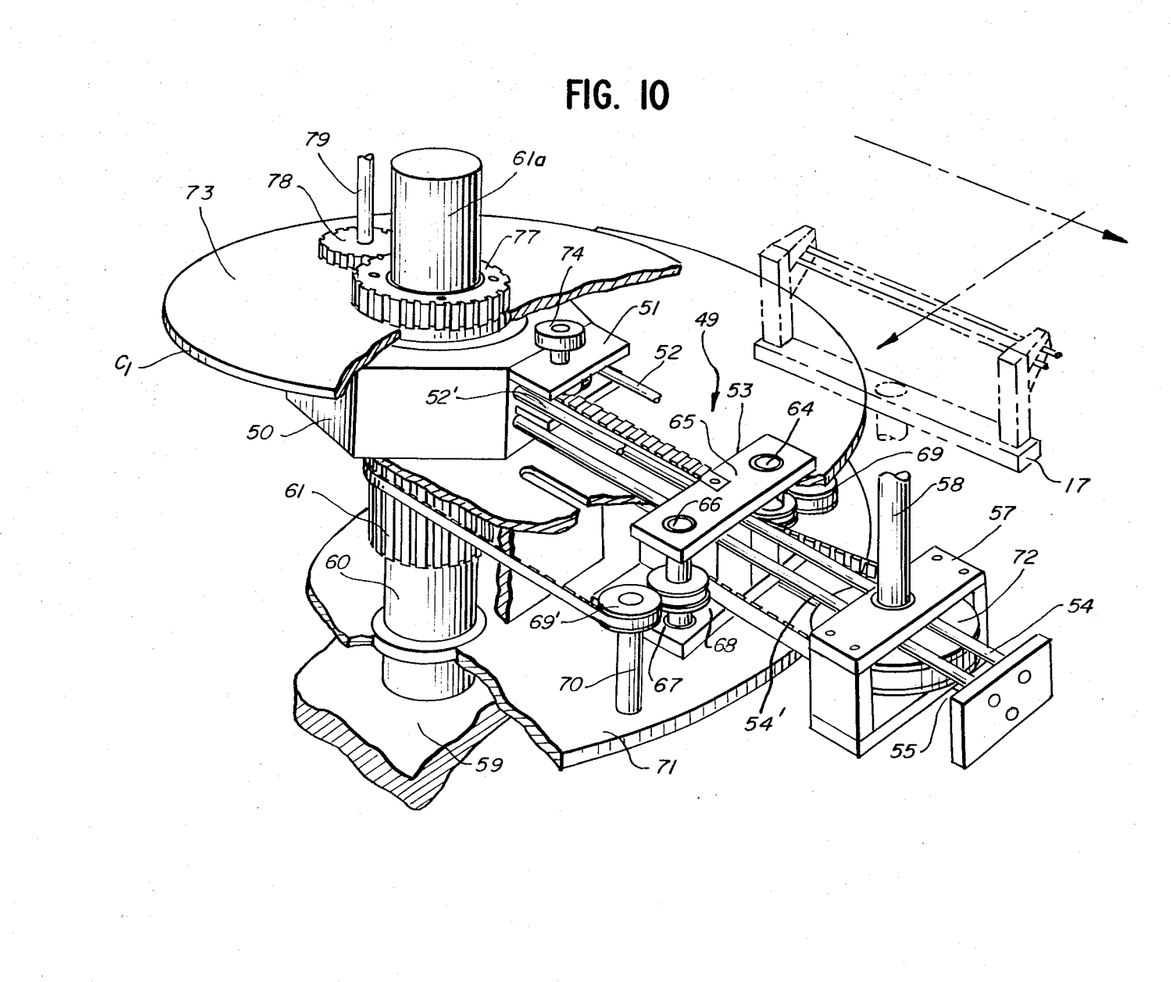
FIG. 10 is a top perspective view similar to FIG. 4 showing the first and second motion modifiers, support rails, and the substructure for the gripper mechanism.
Figure 11:
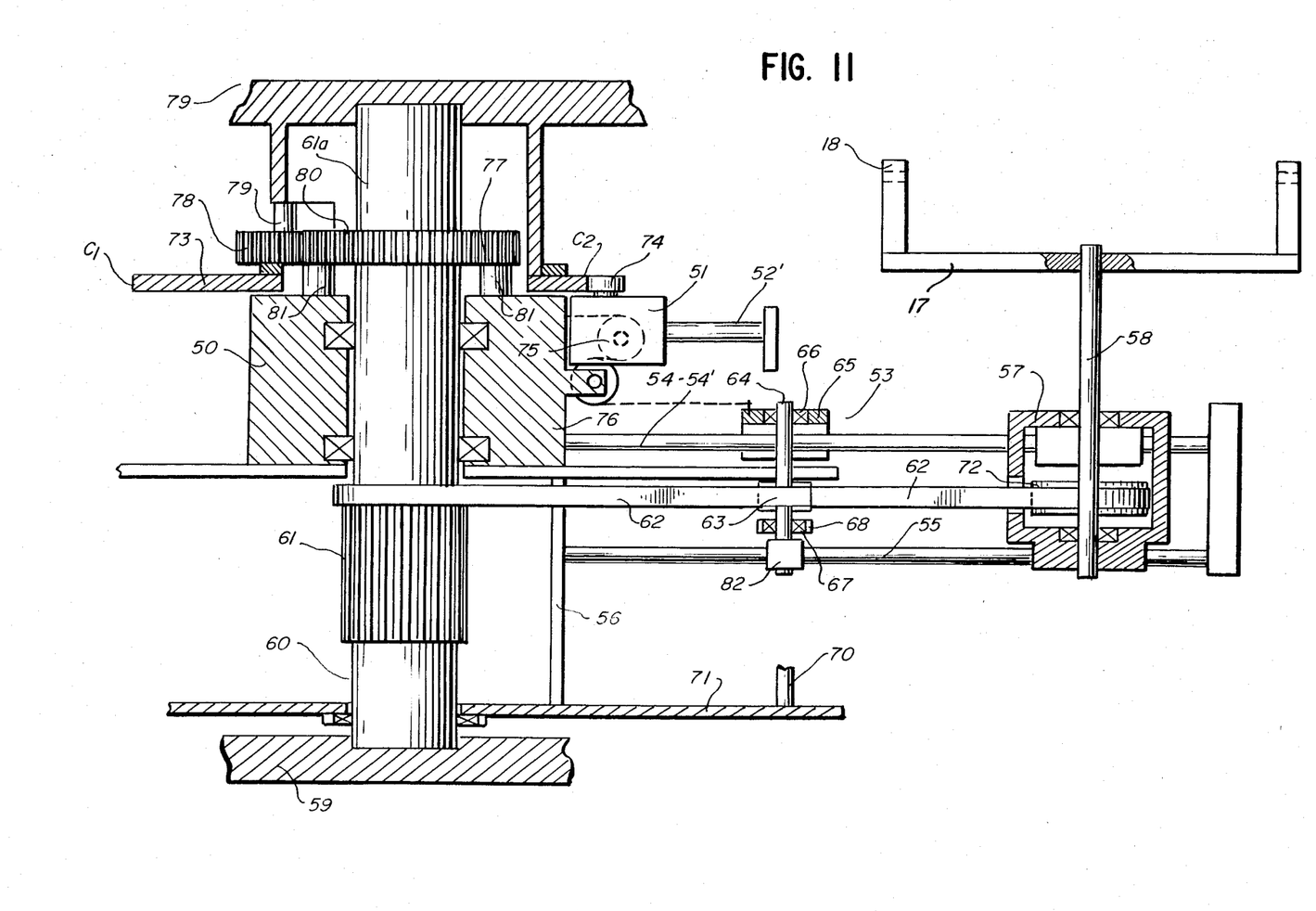
FIG. 11 is a combined side elevation and cross section taken along line 11—11 of FIG. 9 with certain parts crosshatched for clarity and as described herein.

In FIG. 3, one of six radial arms 49 extends from a central hub 50. Each radial arm 49 includes a first motion modifier 51 (see FIGS. 10–11) which is free to slide radially on shafts 52,52'. A second motion modifier 53 (FIGS. 3-10-11) is free to slide radially on two upper shafts 54, 54' which are fixed to the rotating central hub 50, and lower shaft 55 fixed to rotating bracket 56 (FIG. 11). Shaft 55 has an internal magnetized air cylinder piston which is pneumatically biased to maintain tension in belt 62 through a flux-coupled outer member. A third radially slidable structure 57 contains shaft 58 which is rotatable about a vertical axis and which supports gripper assembly 17.

In FIG. 11, certain parts are fixed and non-rotatable. For example, sub-base 59 fixedly holds a non-rotating vertical shaft including fixed stub section 60, fixed pulley section 61 (having vertical timing belt grooves—see FIGS. 4 and 10), and fixed upper section 61a about which the hex shaped hub 50 rotates.

Referring back to FIGS. 3 and 4, the central grooved portion 61 is shown in coacting relationship with a timing belt 62. Pulleys 63 and 63' are parts of slidable motion modifier 53 and are free to rotate about vertical stub shafts 64, 64' which are rotatably held in bearing 66 of top plate 65 and bearing 67 of bottom plate 68 (see also FIG. 11). As seen in FIGS. 9 and 10, coacting timing belt pulleys 69, 69' are mounted on vertical shafts 70, 70' which are fixed to rotating plate 71. The fact that pulley pair 69, 69' are radially fixed and cooperate with radially movable pulley pair 63, 63' is further described and illustrated in FIGS. 6 through 10 which also deal with motion modifiers 51 and 53 and how they continually change the radius of rotation.

Figure 4:
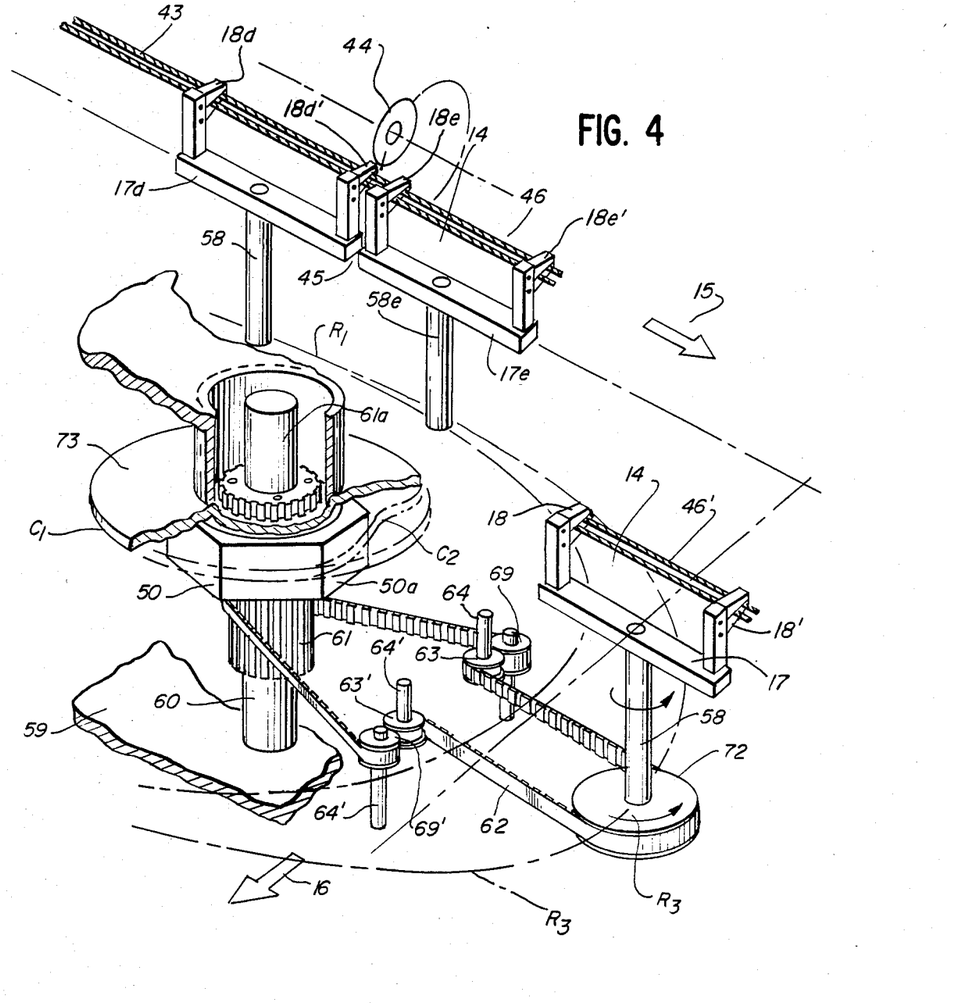
FIG. 4 is a top perspective view of the inventive transfer device with certain parts missing as viewed from the discharge end at the instant of transferring an elastic ribbon pair to a nip between the sealing drum and sealing belt (both not shown)

Referring to FIGS. 3 and 4, the movable motion modifier 53 with attached pulleys 63-63' is shown in general alignment with stationary pulleys 69-69' mounted to rotating plate 71. In essence, whether the small timing pulleys 63 or 69 are mounted for slidable movement or are fixed, they are nonetheless attached to central hex piece 50 or bottom plate 71, both of which rotate relative to the central fixed vertical shaft. In FIGS. 3 and 4, a driven pulley 72 mounted to slidable structure 57 (shown in FIG. 9) and rotatable with respect thereto is also shown as being driven by double sided timing belt 62. In FIG. 3, and assuming rotation of arm 49 downwardly to the position 49' (shown in phantom), belt 62 moves in the direction of arrow 73 relative to idling pulley 69, causing it to rotate counterclockwise. This causes clockwise rotation of idling pulley 63, counter rotation of driven pulley 72, clockwise rotation of idling pulley 63' and counterclockwise rotation of idling pulley 69'. These various pulley rotations are consistent with movement of belt 62 in a direction 74 relative to pulley 69'. In effect, the orientation of gripper assemblies 17d and 17e is maintained parallel to the direction of arrow 15 and when gripper 17e reaches transfer position 14 as at 17, the parallel but spaced elastic ribbons 46' are thus oriented transversely to the direction of web flow while moving parallel to arrow 16. At transfer position 14, these ribbon segments 46' are transferred into the nip between belt system 20 and the vacuum drum 19 of FIG. 1 and are subsequently sealed to the plastic sheet as described hereinabove.

To Vary Radius

FIGS. 3 and 4 deal only with the translation of elastic ribbon segments around a 90° quadrant while maintaining its parallel orientation. However, subsequent illustrations and descriptions define the mechanism and operation of the inventive device as it relates to a simultaneous increase in the radius of rotation about the central shaft 60.

For example, FIGS. 2 shows that while the ribbon segments 46 are being transposed in the lower right hand quadrant, they start at a lesser radius $R_1$ and are transferred from a perpendicular direction (position 14) while traveling at a much larger radius $R_3$ with a subsequent increase in velocity in accordance with the ratio $R_3/R_1$. In a specific example of this beneficial effect, ribbon segments 46 can be cut into length of 6" to 20" while traveling at a velocity of $\omega R$, and, by increasing the radius to $R_3$, can be transferred to the web $W_1$ moving in direction of arrow 16 at a velocity equal to $\omega R_3$ or, in the specific illustration, can be placed such that the repeat distance from one pair of ribbon segments 46' to the next pair of placed ribbons would be 12" to 36". The difference then between 12" to 36" and 6"–20" results in a change in radius of $R_3/R_1$ in the range of about 2:1 to about 3:1. Said differently, the cutoff length for elastic ribbon is in the range of 6" to 20" and by using the illustrated motion modifiers, these stretched ribbons can be placed such that one pair is spread generally in a range of 12" to 36" from the next pair. Subsequent illustrations describe how the increased velocity at an increased diameter is accomplished by the inventive mechanism.

Figure 5:
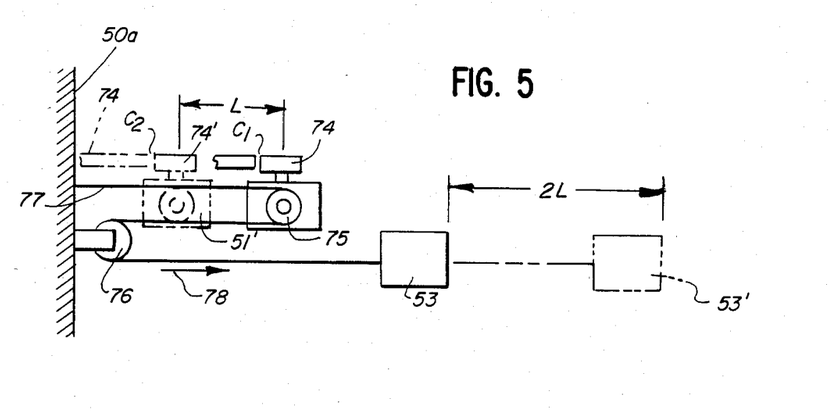
FIG. 5 is a diagramatic illustration of first and second motion modifiers which are used to increase the radius of a rotating arm.

Referring first to FIG. 11, $C_1$ represents the high point of cam 73 (see FIG. 10) and $C_2$ (shown in contact with cam follower 74) is the lower point of the cam. The radial difference between $C_1$ and $C_2$ is, for example, 4". Referring now to FIG. 5, cam follower 74 is shown in solid lines and contacts high point $C_1$ of cam 73. As rotation occurs along the changing cam profile, cam follower 74 is rotated to the low point $C_2$ of cam 73 as shown in the left at 74'. In effect, this causes movement of motion modifier 51 from the solid position at the right to the dotted position 51' at the left. The modifier contains a rotatable pulley 75, and as it moves to the left, belt 77 entrained thereon goes around fixed pulley 76 and will be extended in the direction 78 a length equal to twice the movement of motion modifier 51. The other end of belt 77 is attached to the second motion modifier 53.

In a typical illustration, cam follower movement of 4" causes the first modifier 51 to move 4", but because of te 2:1 belt ratio, causes twice movement to motion modifier 53—in effect a motion doubler. In a specific instance, a 4" cam movement will result in 8" travel of modifier 53 along support rails 54-55".

Figure 6:
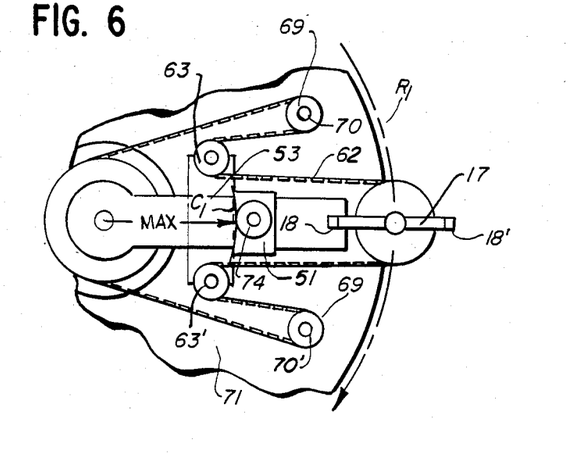
FIGS. 6, 7 and 8 are diagramatic plan views showing various positions of first and second motion modifiers and their positional effect on the radius of the rotating arm.
Figure 7:
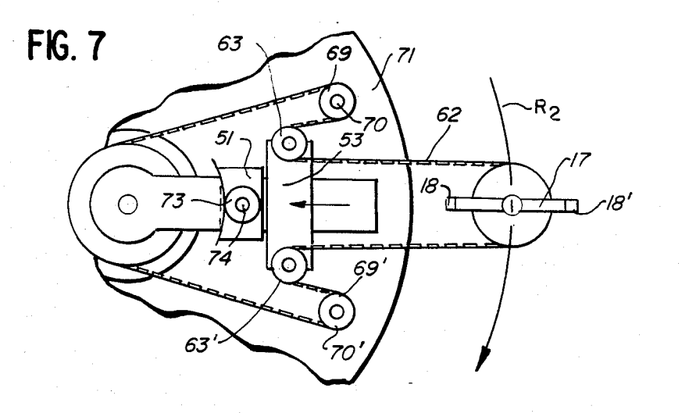
Figure 8:
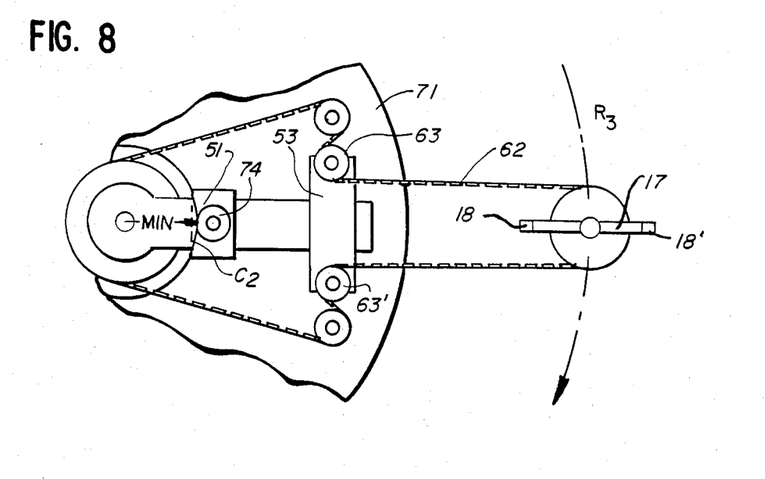
Figure 9:
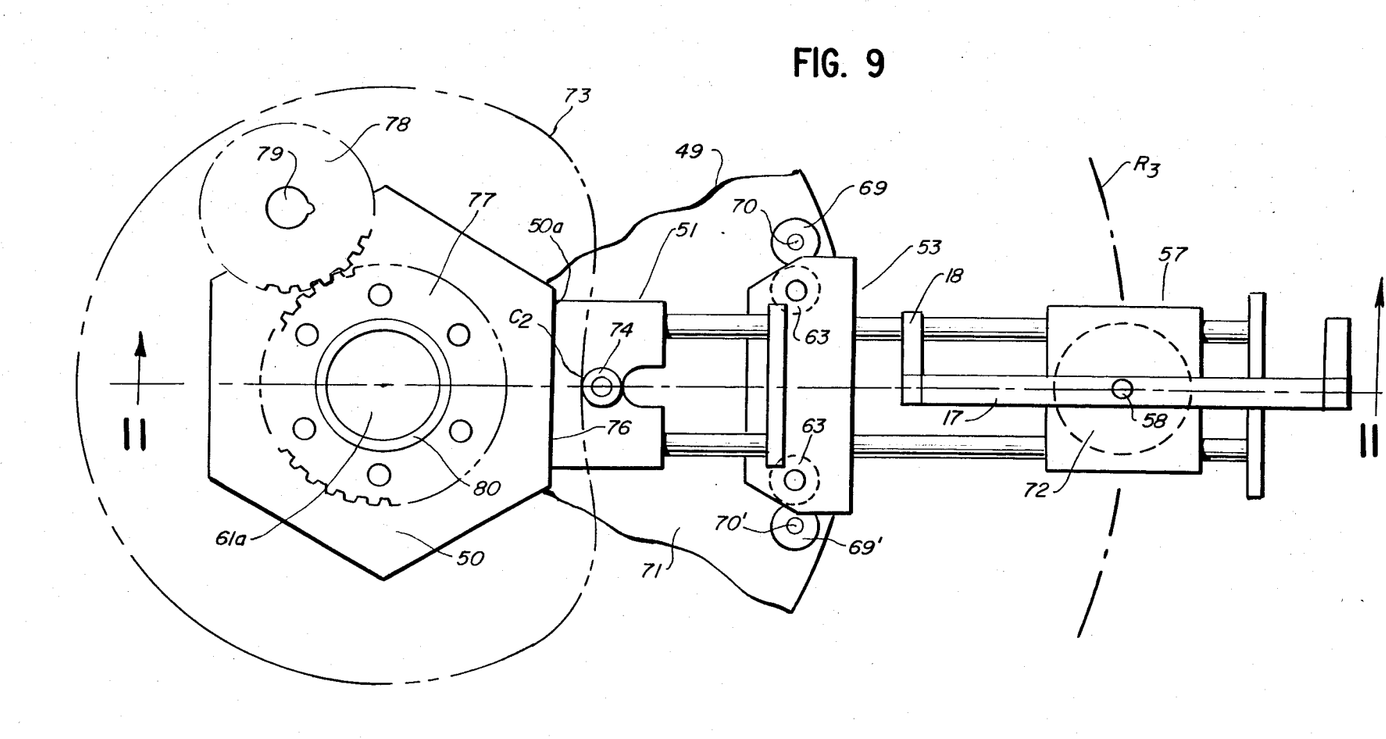
FIG. 9 is a plan view of one of the rotating arms including first and second motion modifiers and the sliding substructure for the gripper device.

Further reference to FIGS. 6 through 8 explain how a further amplification of 2 is achieved to result in a total extension of arm 49 equal to 16". In FIG. 6, cam follower 74 is shown in contact with the high point $C_1$ of cam plate 73 (shown in FIGS. 4, 9 and 11). Note that when the cam follower is on the high point of the cam (shown as maximum cam radius in FIG. 6), the effective transfer radius of gripper assembly 17 is equal to $R_1$.

In FIG. 8, cam follower 74 is shown operating at the low point $C_2$ of the cam plate. This corresponds to the left position 51' of the first motion modifier and the right hand of position 53' of the second motion modifier as shown in FIG. 5. In other words, when the cam follower is operating at the low point of the cam, the extendible arm 49 will be operating at maximum length and transfer radius $R_3$.

In FIGS. 2, 4, 8 and 9, radius $R_3$ is shown as being maximum when the gripper assemblies are ready to transfer the elastic ribbon pair 46' to the drum when operating in a direction parallel to arrow 16. FIG. 7 simply shows an intermediate position whereby cam follower 74 is in contact with cam segment 73 somewhere between the high and low points of the cam.

FIG. 9 is similar to FIG. 8 and shows that with the various motion modifiers 51 and 53 shown as positioned, the structure 57 which supports the gripper assembly 17 via shaft 58 is at the maximum radius $R_3$. FIG. 9 shows a single arm assembly 49 mounted to face 50a of central hub 50, the hub being driven by main gear 77 which in turn is driven by gear 78 keyed to power shaft 79. FIGS. 9 and 11 show gap 80 between fixed shaft section 61a and rotating gear 77.

FIG. 11 clearly shows the non-crosshatched components as being those that are generally supported from, connected to, or rotated with, central hub portion 50. Rotating parts are driven through spacer 81 by top mounted driven gear 77.

Summary of Operation

For the manufacture of a product with a transversely laid down elastic waist band (such as a diaper) the moisture proof outer web is first advanced toward a vacuum drum 19—see FIG. 1. The moisture proof web (advantageously constructed of polyethylene) is indicated by the symbol $W_1$ in the lower right hand corner of FIG. 1 and may be equipped with the usual tape tabs from a web $W_2$. The elastic ribbons ultimately constituting the waist band are designated by the numeral 13 in the lower central portion of FIG. 1 and are seen to follow a path transverse to the direction of movement of web $W_1$. These are ultimately installed in the fashion indicated at 25 in the lower left hand portion of FIG. 2.

Thereafter, the remaining portion of the diaper manufacture is essentially conventional. The web $W_1$ travels with the rotating drum 19 and is equipped with adhesive as at 26—at about the 11 o'clock position of rotation of the drum 19. Thereafter, the leg elastic ribbons 27 and 27' are laid down, these to cause the diaper leg portions to conform to the infant's legs and prevent the escape of urine and fecal matter. The core material, i.e., the fluff pads are designated by the numeral 28 in FIG. 1 and are laid down on the web $W_1$. Thereafter, the final layer $W_4$—non-woven—is laid down followed by the usual cutting and packaging.

The invention is particularly concerned with laying down in stretched form the transverse ribbon 25—see FIG. 2. This is achieved by providing a pair of ribbons 10 (as illustrated) from a source not shown but in the stretched condition as designated by the numeral 43 in the upper right hand portion of FIG. 2. A hub 60 (see also the left hand portion of FIG. 11) carries a plurality of gripping means 17, 17a, 17b, etc. Each gripping means is equipped with spaced apart grippers 18, 18'—still referring to FIG. 2. At a given instant in time, the gripping means 17 are disposed in the condition illustrated in FIG. 2. More particularly, two adjacent gripping means 17d and 17e are gripping lengths of the stretched ribbon 43. When this occurs, a blade severs the ribbons between the adjacent gripping means 17d and 17e—this being illustrated in perspective in the very upper part of FIG. 4 and wherein an orbiting disc blade 44 is schematically illustrated.

As the rotation of the gripping means 17 continues, the gripping means carrying the now-severed ribbon segments proceeds to the position designated 17 in FIG. 2 to underlie the web $W_1$. Concurrently with this the gripping means 17d has proceeded to the position 17e of FIG. 2 and the gripping means 17c has proceeded to the position 17d so as to repeat the concurrent gripping of two continuous lengths of ribbons 43.

In the illustration given, the gripping means are rotated in what might be considered an egg-shaped orbit as illustrated by the dashed line in FIG. 2. In other words, the gripping means 17 in rotating from the three o'clock position to the six o'clock position follow an orbit characterized by an increasing radius. This permits a space advantage wherein the entering ribbons 43 can be close to the hub 60 but where the entering web $W_1$ is spaced somewhat further away in the radial direction.

During the rotation of the gripping means 17, they are maintained always in a configuration parallel to the path followed by the stretched elastic ribbons 43—this being easily perceived from a consideration of FIG. 2. This is achieved through planetary motion developed by motion modifiers seen somewhat schematically fragmentally in FIG. 4.

As a consequence, the gripping means in the position 17—the six o'clock position in FIG. 2—underlies the web $W_1$ which is vacuum held against the drum 19. In other words, the gripping means 17 is radially outward of (lower than) the web $W_1$ when the same is in the condition of being vacuum adhered to the drum 19. Adhesive has been previously applied either to the ribbons or to the web $W_1$ and when the belt 20—see also the left central portion of FIG. 1—engages the ribbon segments and web $W_1$ causing the same to be adhesively united. It will be noted that the width of the belt 20 is less than the distance between the grippers 18 and 18'—see the bottom portion of FIG. 2—to achieve this purpose.

While in the foregoing specification a detailed description of an embodiment of the invention hs been set down for the purpose of illustration, many variations in the details hereingiven may be made by those skilled in the art without departing from the spirit and scope of the invention.

I claim:

1. A method of applying stretched elastic segments to a web as for a diaper waist-band or the like comprising:
    advancing at least one continuous stretched elastic ribbon along a first linear path,
    gripping said ribbon at two pairs of points spaced longitudinally in said first path,
    severing said ribbon between said pairs of points to provide a stretched ribbon segment between one pair of points and a portion of said continuous ribbon between the other pair of points,
    advancing the ribbon segment along a portion of an orbital path while maintaining the length of said segment parallel to said first linear path, and
    adhesively uniting said segment to a continuous web being advanced in a second linear path generally perpendicular to said first linear path.

2. The method of claim 1 in which said orbital path has an increasing radius between the points of severance and adhesively uniting.

3. The method of claim 1 in which the step of adhesively uniting includes pressing said segment against said continuous web while said web is vacuum held against a drum.

4. A method of applying stretched elastic segments transversely aligned to a moving web comprising the steps of:
    advancing a substrate web in a first horizontal direction,
    advancing a parallel pair of stretched continuous elastic ribbons in a second horizontal direction perpendicular to said first direction and placing adhesive on one of said web and ribbons,
    rotating a gripping means about a vertical axis while maintaining orientation of said gripping means parallel to the second direction,
    gripping said parallel elastic ribbons at the leading and trailing ends of two spaced consecutive portions,
    severing said ribbon pair in the space between consecutive gripping means to provide a pair of ribbon segments,
    advancing a parallel pair of segments along a generally arcuate path while maintaining orientation of the same transverse to said first direction,
    transferring said segments from said gripping means to said substrate at a location approximately 90° from the position of ribbon severing,
    advancing said substrate web with said transversely placed segments on the peripheral surface of a drum rotating about a horizontal axis, said drum cooperating with belt means to contain said substrate web and segments therebetween,
    advancing said substrate and adhesively bonded segments beyond said belt containment means and severing said substrate web in the space between adjacent pairs of elastic segments to form a discreet article whereby said elastic segments are adapted to gather predetermined portions of said article in said transverse direction.

5. The method of claim 4 wherein said arcuate path is non-circular and curvilinear.

6. The method of claim 5 wherein the radius of said arcuate path changes during a partial orbit of said gripping means about a central shaft.

7. The method of claim 5 wherein the non-circular portion of the path extends beyond the point of transferring elastic to substrate.

8. The method of claim 1 wherein the center of rotation of said gripping means changes during a portion of its orbital path about a central shaft.

9. The method of claim 1 wherein maintaining a fixed orientation of the elastic relative to the substrate is achieved by using a belt-pulley rotational system.

10. The method of claim 9 wherein maintaining the fixed orientation is achieved with a belt system coacting with planetary gears.

11. Apparatus for applying stretched elastic segments to a web for diaper waist-bands and the like comprising:
means for advancing at least one continuous stretched elastic ribbon along a first linear path, a pedestal adjacent said first linear path and equipped with a plurality of circumferentially spaced gripping means, each gripping means including a pair of spaced apart grippers adapted to grip said ribbon at two points spaced therealong,
means operatively associated with said pedestal for rotating said gripping means to bring said successive gripping means into engagement with said ribbon at spaced points,
a cutting means adjacent said first linear path for cutting said ribbon between said successive gripping means to provide a discreet ribbon segment,
said rotating means being operative to rotate said gripping means on an increasing radius through an arc of about 90° and while maintaining said gripping means in a predetermined orientation to maintain said segment parallel to said first linear path,
means for advancing a continuous web along a linear path generally perpendicular to said first linear path, and
a belt equipped drum in said second path, said belt cooperating with said drum to press said segment against said web.

12. The apparatus of claim 11 in which means are provided adjacent one of said paths for applying adhesive to one of said web and ribbon.

13. The apparatus of claim 11 in which said rotating means includes a motion modifier to maintain said segment parallel to said first linear path.

14. The apparatus of claim 13 in which said rotating means includes two motion modifiers.

15. The apparatus of claim 13 in which said rotating means includes a cam system in combination with said motion modifier for increasing the radius of rotation of said gripping means.

* * * * *